US006982288B2

(12) United States Patent
Mitra et al.

(10) Patent No.: US 6,982,288 B2
(45) Date of Patent: Jan. 3, 2006

(54) MEDICAL COMPOSITIONS CONTAINING AN IONIC SALT, KITS, AND METHODS

(75) Inventors: Sumita B. Mitra, West Saint Paul, MN (US); Afshin Falsafi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 469 days.

(21) Appl. No.: 10/121,329

(22) Filed: Apr. 12, 2002

(65) Prior Publication Data

US 2003/0195273 A1    Oct. 16, 2003

(51) Int. Cl.
*A61K 6/083* (2006.01)
*A61C 5/00* (2006.01)

(52) U.S. Cl. .................. 523/119; 523/116; 523/120; 522/71; 524/236; 524/414; 524/423; 526/173; 526/220; 526/227; 526/236; 526/318.4; 433/228.1

(58) Field of Classification Search ................ 526/173, 526/220, 227, 236, 318.4; 523/119; 522/71; 524/236, 414, 423; 433/228.1
See application file for complete search history.

(56) References Cited

U.S. PATENT DOCUMENTS

| | | | |
|---|---|---|---|
| 3,505,290 A | | 4/1970 | Mazzolini et al. |
| 3,763,121 A | * | 10/1973 | Schnafke et al. ........... 526/331 |
| 3,836,512 A | * | 9/1974 | Chu ........................... 526/207 |
| 4,209,434 A | | 6/1980 | Wilson et al. |
| 4,254,005 A | | 3/1981 | Rowland et al. |
| 4,503,169 A | | 3/1985 | Randklev |
| 4,695,251 A | | 9/1987 | Randklev |
| 4,872,936 A | | 10/1989 | Engelbrecht |
| 4,900,697 A | | 2/1990 | Akahane et al. |
| 5,130,347 A | | 7/1992 | Mitra |
| 5,154,762 A | | 10/1992 | Mitra et al. |
| 5,264,278 A | * | 11/1993 | Mazurek et al. ......... 428/317.3 |
| 5,292,842 A | * | 3/1994 | Yang ....................... 526/318.4 |
| 5,501,727 A | | 3/1996 | Wang et al. |
| 5,520,725 A | | 5/1996 | Kato et al. |
| 5,814,682 A | | 9/1998 | Rusin et al. |
| 5,824,720 A | | 10/1998 | Nowak et al. |
| 2003/0134933 A1 | * | 7/2003 | Jin et al. |
| 2003/0166740 A1 | * | 9/2003 | Mitra et al. |

FOREIGN PATENT DOCUMENTS

| | | |
|---|---|---|
| WO | WO 97/00065 | 1/1997 |
| WO | WO 99/03444 | 1/1999 |

* cited by examiner

*Primary Examiner*—Tae H. Yoon
(74) *Attorney, Agent, or Firm*—Sean Edman

(57) ABSTRACT

A hardenable medical composition (preferably, dental composition) that includes an ionic redox polymerization system and at least one secondary ionic salt that includes a cation selected from the group consisting of a Group I ion, a Group II ion, an ammonium ion of the formula $NR_4^+$ wherein each R is H or a (C1–C4)alkyl group, and mixtures thereof.

45 Claims, No Drawings

MEDICAL COMPOSITIONS CONTAINING AN IONIC SALT, KITS, AND METHODS

TECHNICAL FIELD

This invention relates to hardenable medical (preferably, dental) compositions containing one or more ionic salts. Such compositions are preferably dental compositions, such as cements, filling materials, adhesives, etc. This invention relates particularly to water-based dental cements.

BACKGROUND

Resin-based composite and restorative materials generally have very high cohesive strength, and accordingly are widely used in dentistry. Cements are used in dental materials as lining cements, luting cements, or for affixing orthodontic devices. Resin-based cements are utilized primarily for bonding of appliances such as veneers, inlays, onlays, crowns, and bridges. Resin cements generally provide excellent physical properties such as high compressive and tensile strength and low solubility, and are often used for bonding in difficult indirect bonding situations such as non-parallel or short crown preps. Generally, these cements are used in conjunction with dentin bonding agents to assure retention of the prosthodontic device. Another important class of curable dental materials is water-based resin-modified ionically hardenable cement. Cements of this category typically do not require additional adhesive. These cements have excellent biocompatibility, prevent or minimize post operative sensitivity, and are easy to clean up. Some of these cements, particularly the glass ionomer cements, also provide long-term fluoride release associated with cariostatic behavior.

Restorative filling materials are closely related to the cements mentioned above in chemical composition. In contrast to cements, however, restorative filling materials are more highly filled to provide higher viscosity, mechanical properties, and wear resistance. The setting characteristics should allow sufficient time for mixing the material to the restoration or tooth preparation and for seating the prosthodontic or orthodontic device in place in the mouth. Both resin based composites and water-based cements can be used as restorative filling materials if properly formulated.

The materials described above are available as multi-part systems, typically in two-parts. These can be in any combination of powder, liquid, or paste. Shelf stability of the individual parts is extremely important so that there is no change in viscosity, color or any other property occurring during the shelf life of the material (typically 2–4 years). In use, the parts are mixed together and then applied. Setting should occur in a short period of time so that the procedure is not uncomfortable for the patient or the operator. The setting characteristics should allow for sufficient time for mixing the materials and applying to the tooth preparation and/or prosthodontic or orthodontic device in place in the mouth.

Certain additives are used in such compositions in order to improve stability; however, some useful additives also alter the setting characteristics unpredictably, provide adverse colorants, alter the viscosity, or generate potential toxic or narcotic by-products. Thus, there is a need for compositions that are more medically acceptable.

SUMMARY OF THE INVENTION

The present invention provides a hardenable (e.g., curable by polymerization, crosslinking, ionic reaction, or other chemical reaction) composition that includes an ionic redox polymerization system and one or more secondary ionic salts. Such compositions are particularly useful in medical applications (which includes dental applications), such as orthopedic cements, orthodontic cements, dental sealants, dental adhesives, dental cements, dental restoratives, and dental prostheses, for example. As used herein, "a" or "an" means "at least one" or "one or more" unless otherwise indicated.

Such compositions are advantageous because they have enhanced stability, e.g., shelf life stability, over compositions lacking a secondary ionic salt. The hardenable composition can be used in a wide variety of applications, preferably dental applications, that do not require the use of a curing light. Additionally, a curing light can be used if desired when a photoinitiator is present in the hardenable composition.

The "secondary ionic salt" is a salt that dissociates in solution into its corresponding anion(s) and cation(s), the ionic salt being secondary in the sense that it is in addition to other ionic components, e.g., redox catalysts that may be present in the composition. The secondary ionic salt is "non-interfering" or "non-reactive." By this is meant that the secondary ionic salt is not reactive with any of the other components in the composition such that it could interfere with the function of the composition. That is, the secondary ionic salt should not interfere with the hardenable resin system by either causing premature hardening or lack of hardening when desired. For example, the secondary ionic salt should not interfere with the ionic redox polymerization system (either causing premature polymerization or preventing desired polymerization) nor should the secondary ionic salt react undesirably with the acid-functional component or the resin system, if present. More than one secondary ionic salt may be needed for optimum performance of certain compositions.

The invention, in one embodiment, provides a hardenable medical composition (e.g., an adhesive or a sealant) that includes: a hardenable resin system including an ethylenically unsaturated component and preferably an acid-functional component; water; an ionic redox polymerization system; and a secondary ionic salt that includes a cation selected from the group consisting of a Group I ion, a Group II ion, an ammonium ion of the formula $NR_4^+$ wherein each R is H or a (C1–C4)alkyl group, and mixtures thereof.

The invention, in another embodiment, provides a hardenable medical composition (preferably a dental composition such as a dental sealant, dental adhesive, dental cement, dental restorative, or a dental prostheses) that includes: a hardenable resin system including an ethylenically unsaturated component and preferably an acid-functional component; water; a filler; an ionic redox polymerization system; and a secondary ionic salt that includes a cation selected from the group consisting of a Group I ion, a Group II ion, an ammonium ion of the formula $NR_4^+$ wherein each R is H or a (C1–C4)alkyl group, and mixtures thereof.

For preferred embodiments, the ionic salt includes a Group Ia ion (e.g., sodium, lithium, potassium, cesium). For more preferred embodiments, an ion of the secondary salt is the same as an ion of the redox system.

The ionic redox polymerization system can includes an ionic oxidizing agent, an ionic reducing agent, or both. The reducing agent can be polymerizable or nonpolymerizable. Preferably, the reducing agent includes urea or thiourea functionality.

A preferred group of nonpolymerizable reducing agents include 1-ethyl-2-thiourea, tetraethyl thiourea, tetramethyl thiourea, 1,1-dibutyl thiourea, and 1,3-dibutyl thiourea. A preferred group of polymerizable reducing agents include 5-acryloxyalkyl barbituric acid, 5-allyl 5-isopropyl barbituric acid, 5-ethyl 5-crotyl barbituric acid, a (meth)acryloxyalkyl thiourea, 1-allyl thiourea, 1,1-diallyl thiourea, 1,3-diallyl thiourea, 1-allyl-3-(2-hydroxyethyl)-2-thiourea, and 1-allyl-3-methyl thiourea.

The ethylenically unsaturated component can be in the form of a monomer, oligomer, polymer, or combination thereof. Similarly, the optional acid-functional component can be in the form of a monomer, oligomer, polymer, or combination thereof. The acid-functional component and the ethylenically unsaturated component can be the same component. That is, one compound can be used that has both acidic functionality and ethylenic unsaturation. Alternatively, the ethylenically unsaturated component is distinct from the acid-functional component.

Preferably, if present, the acid-functional component includes a homopolymer or copolymer of alkenoic acids. For certain embodiments, the acid-functional component and ethylenically unsaturated component are the same component.

In a particularly preferred embodiment, the present invention provides a hardenable dental composition (e.g., a dental sealant, dental adhesive, dental cement, dental restorative, or a dental prostheses) that includes: a hardenable resin system including an ethylenically unsaturated component and an acid-functional component; water; an acid-reactive filler; an ionic redox polymerization system comprising an ionic oxidizing agent; and a secondary ionic salt comprising a cation selected from the group consisting of a Group I ion, a Group II ion, an ammonium ion of the formula $NR_4^+$ wherein each R is H or a (C1–C4)alkyl group, and mixtures thereof.

In another particularly preferred embodiment, the present invention provides a hardenable dental composition that includes: a hardenable resin system including an ethylenically unsaturated component; water; an ionic redox polymerization system comprising an ionic oxidizing agent, a reducing agent comprising a urea or thiourea functional group; and a secondary ionic salt comprising a cation selected from the group consisting of a Group I ion, a Group II ion, an ammonium ion of the formula $NR_4^+$ wherein each R is H or a (C1–C4)alkyl group, and mixtures thereof.

The present invention also provides kits that include one or more containers whose contents collectively include the hardenable compositions described herein.

The present invention also provides methods of making and using the hardenable compositions described herein. For example, the hardenable compositions of the present invention can be used in methods of adhering or cementing (either intraorally or extraorally) a dental article (e.g., crown, bridge, orthodontic appliance) to a tooth or bone, as well as in methods of filling a tooth.

Preferably, the hardenable composition includes a glass ionomer composition that may include two or more parts in any combination of powder, liquid, or paste. The hardenable composition is water-based, and thus can be used under moist conditions such as are typically present in the mouth.

DETAILED DESCRIPTION OF PREFERRED EMBODIMENTS

The medical compositions of the present invention include a hardenable resin system, water, an ionic redox polymerization system, and one or more secondary ionic salt. The ionic redox polymerization system includes an oxidizing agent and a reducing agent that can be either polymerizable or nonpolymerizable. The reducing agents and oxidizing agents are selected such that they are miscible in the compositions, and preferably, such that they are also miscible in water.

The medical compositions of the present invention are water-based. Water-based systems containing active redox agents have typically low shelf-stability, especially in the presence of acidic components and polymerizable moieties. However, the incorporation of a secondary ionic salt has provided surprisingly enhanced stability, e.g., shelf life stability, over the same compositions lacking a secondary ionic salt.

Thus, the compositions of the present invention are advantageous because they have enhanced stability, e.g., shelf life stability, over compositions lacking a secondary ionic salt. Preferably, such compositions display an increase in shelf life of at least about 10 times, preferably at least about 100 times, at 37° C. according to the procedure of the Storage Stability Test in the Examples Section.

The resin system typically includes one or more ethylenically unsaturated monomers, oligomers, or polymers, as will be described below. The resin system can also preferably include one or more acid-functional monomers, oligomers, or polymers, as will be described below.

The hardenable compositions can be used in a variety of medical applications, including dental applications, but particularly dental applications. When used in dental applications, such as dental adhesives, dental cements, and dental filling materials, for example, the hardenable (typically, curable) composition may bond directly to dental enamel and/or dentin. Alternatively, a primer layer can be used on the dental enamel and/or dentin on which the hardenable composition is used.

The compositions of the invention can harden by undergoing one or more of a number of reactions. At least one of the mechanisms of hardening involves a redox reaction. The redox mechanism can be supplemented with a light-cure mechanism if a photoinitiator is present. Alternatively or additionally, the redox mechanism can be supplemented with an ionic hardening mechanism. By this is meant that the compositions contain ingredients that, when combined, can react via an ionic reaction to produce a hardened mass.

Resin System

The components of the resin system are selected such that they are miscible with the other components of the hardenable composition. That is, preferably, the components of the resin system are at least sufficiently miscible that they do not undergo substantial sedimentation when combined with the other ingredients of the composition (e.g., reducing agent and oxidizing agent). Preferably, the components of the resin system are miscible with water. The components of the resin system can be monomers, oligomers, polymers, or combinations thereof.

The resin systems of the hardenable compositions of the present invention typically include an ethylenically unsaturated component. Preferably, the resin systems of the hardenable compositions of the present invention also include an acid-functional component. The ethylenically unsaturated component can be present as a separate ingredient or the ethylenic unsaturation can, if desired, be present as a moiety in another compound such as the acid-functional component. In this way, one compound can include an acid-functional portion and an ethylenically unsaturated portion.

In one embodiment, the ethylenically unsaturated component includes α,β-unsaturated compounds. Preferred α,β-unsaturated compounds can provide altered properties such as toughness, adhesion, set time, and the like. When α,β-unsaturated compounds are employed, they preferably are water-soluble, water-miscible, or water-dispersible. Water-soluble, water-miscible, or water-dispersible (meth)acrylates (i.e., acrylates and methacrylates), (meth)acrylamides (i.e., acrylamides and methacrylamides), and urethane (meth)acrylates are preferred. Examples include, but are not limited to, 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, triethylene glycol dimethacrylate, bisGMA, ethoxylated bisphenolA diacrylate, ethoxylated bisphenolA dimethacrylate, polyethylene glycol dimethacrylate, acrylamide, methacrylamide, methylene bis-acrylamide, methylene bis-methacrylamide, diacetone acrylamide, and diacetone methacrylamide. Suitable ethylenically unsaturated compounds are also available from a wide variety of commercial sources, such as Sigma-Aldrich, St. Louis, Mo. and Rhom and Tech, Inc., Darmstadt, Germany. Mixtures of $\alpha,\beta$-unsaturated compounds can be used if desired.

Preferred compositions of the present invention include a sufficient quantity of ethylenically unsaturated component to provide the desired setting or hardening rate and desired overall properties following hardening. Preferably, the mixed but unset hardenable compositions of the invention contain at least about 1 percent by weight (wt-%), more preferably at least about 5 wt-%, and most preferably at least about 10 wt-%, of an ethylenically unsaturated component, based on the total weight (including water) of the hardenable (mixed but unset) composition.

The acid-functional component can include monomers, oligomers, or polymers and can include oxyacid functional derivatives of carbon, phosphorous, sulfur, and boron compounds. Suitable acid-functional compounds include those listed at column 2, line 62 through column 3, line 6 of U.S. Pat. No. 4,209,434 (Wilson et al.). Preferred acid-functional compounds are polymers, including homopolymers and copolymers (i.e., of two or more different monomers), of alkenoic acids such as acrylic acid, 2-chloroacrylic acid, 2-cyanoacrylic acid, aconitic acid, citraconic acid, fumaric acid, glutaconic acid, itaconic acid, maleic acid, mesaconic acid, methacrylic acid, and tiglic acid. Mixtures of acid-functional compounds can be used if desired.

As will be appreciated by those skilled in the art, the acid-functional component should have a molecular weight sufficient to provide good storage, handling, and mixing properties. A preferred molecular weight for a acid-functional component is about 60 to about 100,000 weight average molecular weight as evaluated using gel permeation chromatography and a polystyrene standard, with about 80 to about 30,000 being most preferred.

Preferred compositions of the present invention include a sufficient quantity of an acid-functional component to provide the desired setting characteristics and desired overall properties following hardening. Preferably, the mixed but unset hardenable compositions of the invention contain at least about 2 percent by weight (wt-%), more preferably at least about 5 wt-%, and most preferably at least about 10 wt-% of an acid-functional component, based on the total weight (including water) of the hardenable (mixed but unset) composition.

As stated above, in an alternative embodiment, the ethylenic unsaturation can be present as a moiety in the acid-functional component. For example, $\alpha,\beta$-unsaturated acidic compounds such as glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Fillers

The hardenable compositions of the present invention can also contain fillers. Fillers may be selected from one or more of a wide variety of materials suitable for incorporation in compositions used for medical (e.g., dental) applications, such as fillers currently used in dental restorative compositions, and the like. The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler is also substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and colloidal and submicron silica particles (e.g., pyrogenic silicas such as those available under the trade designations AEROSIL, including "OX 50", "130", "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

Preferably, the average particle size (typically, diameter) for the FAS glass is no greater than about 10 micrometers, and more preferably no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used either in the same part or in different parts.

The amount of filler should be sufficient to provide a hardenable composition having desirable mixing and handling properties before hardening, and good performance after hardening. Preferably, the filler represents no greater than about 90 wt-%, more preferably no greater than about 85 wt-%, and most preferably no greater than about 80 wt-%, of the total weight (including water) of the hardenable composition components. Preferably, the filler represents at least about 1 wt-%, more preferably at least about 5 wt-%, and most preferably at least about 30 wt-%, of the total weight (including water) of the hardenable composition components.

Ionic Redox Polymerization System

The ionic redox polymerization system includes at least one reducing agent and at least one oxidizing agent, wherein at least one of the reducing agents or oxidizing agents is ionic. That is, at least one of the reducing agents or oxidizing agents releases ions in water.

The reducing and oxidizing agents are conveniently discussed together. They should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

The reducing agents of the present invention include a reducing agent that may or may not be polymerizable. Combinations of two or more reducing agents may be used to provide an optimum balance of working and setting characteristics as well as the final properties of the cured material. The reducing agents can be in the form of a monomer, oligomer, or polymer. Preferably, the reducing agent has a water solubility of at least about 2 wt-% at room temperature.

Suitable nonpolymerizable reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline, N,N-dihydroxyethyl p-toluidine, 4-dimethylaminophenylethanol, triethylamine, 3-dimethylamino benzoic acid, and ethyl dimethylaminobenzoate; barbituric acid derivatives, such as 1-benzyl-5-phenyl barbituric acid and 5-butyl barbituric acid; and aromatic sulfinic salts, such as p-toluenesulfinic salts and benzenesulfinic salts. A particularly desirable nonpolymerizable reducing agent includes a urea or thiourea functionality (see below), and preferably a thiourea functional group. Examples of such compounds include 1-ethyl-2-thiourea, tetraethyl thiourea, tetramethyl thiourea, 1,1-dibutyl thiourea, and 1,3-dibutyl thiourea. Other nonpolymerizable reducing agents may include cobalt (II) chloride, ferrous chloride, ferrous sulfate, hydrazine, hydroxylamine (depending on the choice of oxidizing agent), oxalic acid, and salts of a dithionite or sulfite anion. Various mixtures of nonpolymerizable reducing agents can be used if desired.

Preferably, the reducing agent is polymerizable. The polymerizable reducing agent includes a urea or thiourea group of the following structure,

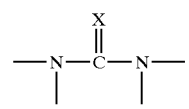

wherein X is oxygen (O) or sulfur (S). When X is O, the reducing agent includes a urea group. Alternatively, when X is S, the reducing agent includes a thiourea group. Urea and thiourea groups are known to function as reductants in oxidation-reduction (i.e., redox) polymerization reactions. In addition, derivatives of urea and thiourea are also useful as polymerizable reducing agents. Various combinations of such polymerizable reducing agents can be used if desired.

Urea compounds include, for example, derivatives of barbituric acid such as 5-acryloxyalkyl barbituric acid, 5-allyl 5-isopropyl barbituric acid, and 5-ethyl 5-crotyl barbituric acid.

Another class of polymerizable reducing agents is acrylated tertiary amines, e.g., 2-dimethylaminoethyl (meth) acrylate.

Preferably, the polymerizable reducing agent includes an allyl thiourea group, as it is acid stable and prevents the formation of coloration often encountered with amine-containing reducing agents or with ascorbic acid. Preferred polymerizable reducing agents that include an allyl thiourea group include an acryloxyalkyl thiourea, 1-allyl thiourea, 1,1-diallyl thiourea, 1,3-diallyl thiourea, 1-allyl-3-(2-hydroxyethyl)-2-thiourea, and 1-allyl-2-methyl thiourea. A most preferred polymerizable reducing agent that includes an allyl thiourea group is represented by the following structure:

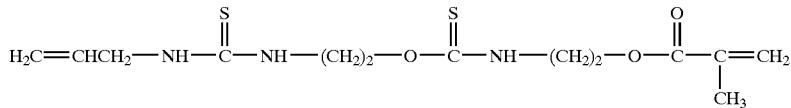

Various combinations of reducing agents can be used, whether they be polymerizable or nonpolymerizable. When the reducing agent is polymerizable, a secondary reducing agent is preferably used as well. Such secondary reducing agents can be polymerizable or nonpolymerizable and may be selected from the groups of polymerizable and nonpolymerizable reducing agents listed herein.

Typically, with the use of the polymerizable urea or thiourea reducing agent and a secondary reducing agent, significant advantages can be realized. This combination provides a balance of properties with respect to color stability of both the hardenable and hardened compositions, toxicity of the hardened composition, and reaction time ("snap set") of the hardenable composition, along with the shelf stability of the components of the hardenable composition.

Suitable oxidizing agents will also be familiar to those skilled in the art, and include, but are not limited to, persulfuric acid and salts thereof such as sodium, lithium, potassium, ammonium, cesium, and alkyl ammonium salts. Additional oxidizing agents include peroxides such as benzoyl peroxides, hydroperoxides such as cumyl hydroperoxide, t-butyl hydroperoxide, sodium peroxide, hydrogen peroxide, and amyl hydroperoxide, as well as salts of transition metals such as cobalt (III) chloride, ferric chloride, cerium (IV) sulfate, perboric acid and salts thereof, permanganic acid and salts thereof, and perphosphoric acid and salts thereof (depending upon the choice of reducing agent).

It may be desirable to use more than one oxidizing agent or more than one reducing agents. Small quantities of transition metal compounds may also be added to accelerate the rate of redox cure.

The reducing and oxidizing agents are present in an amount sufficient to permit an adequate free-radical reaction rate. This can be evaluated by combining all of the ingredients of the hardenable composition except for the optional filler, and observing whether or not a hardened mass is obtained.

Preferably, the reducing agent is present in an amount of at least about 0.01 wt-%, and more preferably at least about 0.1 wt-%, based on the total weight (including water) of the components of the hardenable composition. Preferably, the reducing agent is present in an amount of no greater than about 10 wt-%, and more preferably no greater than about 5 wt-%, based on the total weight (including water) of the components of the hardenable composition.

Preferably, an optional secondary reducing agent is present in an amount of at least about 0.01 wt-%, and more preferably at least about 0.05 wt-%, based on the total weight (including water) of the components of the hardenable composition. Preferably, the optional secondary reducing agent is present in an amount of no greater than about 10 wt-%, and more preferably no greater than about 5 wt-%, based on the total weight (including water) of the components of the hardenable composition.

Preferably, the oxidizing agent is present in an amount of at least about 0.01 wt-%, and more preferably at least about 0.10 wt-%, based on the total weight (including water) of the components of the hardenable composition. Preferably, the oxidizing agent is present in an amount of no greater than about 10 wt-%, and more preferably no greater than about 5 wt-%, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with the acid-functional component and optional filler and kept in a storage-stable state. Likewise, through appropriate selection of a water-insoluble encapsulant, the reducing and oxidizing agents can be combined with the FAS glass and water and maintained in a storage-stable state.

Preferably the encapsulant is a medically acceptable polymer and a good film former. Also, the glass transition temperature (Tg) of the encapsulant preferably is above room temperature.

Secondary Ionic Salt

The secondary ionic salt is "non-interfering" or "non-reactive." By this is meant that the secondary ionic salt is not reactive with any of the other components in the composition such that it could interfere with the function of the composition. That is, the secondary ionic salt should not interfere with the hardenable resin system by either causing premature hardening or lack of hardening when desired. For example, the secondary ionic salt should not interfere with the ionic redox polymerization system (either causing premature polymerization or preventing desired polymerization) nor should the secondary ionic salt react undesirably with the acid-functional component, if present.

Examples of interfering salts that would be unsuitable as secondary ionic salts of the present invention include acid-reactive salts, such as metal salts, e.g., calcium chloride, magnesium chloride, barium nitrate, calcium nitrate, magnesium nitrate, and calcium fluoroborate; salts of aluminum, iron, and tin; salts used in association with photoinitiator systems, and salts that are themselves reducing agents or oxidizing agents, e.g., sodium benzene sulfinate.

The secondary ionic salt includes one or more of an ammonium ion of the formula $NR_4^+$, where each R is independently H or a (C1–C4)alkyl group, a Group I ion, a Group II ion, or mixtures thereof. As used herein, an ionic component is one that releases ions in water. Preferably, the secondary ionic salt includes a Group Ia ion (lithium, sodium, potassium, or cesium). For particularly preferred embodiments, a cation of the secondary ionic salt is the same as a cation of the ionic redox polymerization system.

Suitable anions that can be combined with one or more of the cations discussed above include, for example, sulfate, nitrate, halide, carbonate, tetrafluroborate, and phosphate. The secondary ion salts can also include hydrogen atoms as ionic salts containing hydrogen sulfate, hydrogen phosphate, bicarbonate, and dihydrogen phosphate.

Preferably, the secondary ionic salt has a water solubility of at least about 2 wt-% (weight percent), and more preferably at least about 5 wt-%, at room temperature.

Examples of preferred secondary ionic salts include sodium and potassium sulfate, sodium and potassium hydrogen sulfate, sodium and potassium phosphate, disodium and dipotassium hydrogen phosphate, and sodium and potassium dihydrogen phosphate. Examples of more preferred secondary ionic salts include potassium sulfate and potassium dihydrogen phosphate.

Any compatible combination of two or more secondary ionic salts can also be used in the present invention. For example, the compositions of the present invention can include a combination of potassium sulfate and potassium dihydrogen phosphate.

Preferably, the secondary ionic salt is present in an amount of at least about 0.02 wt-%, and more preferably at least about 0.1 wt-%, based on the total weight (including water) of the components of the hardenable composition. Preferably, the secondary ionic salt is present in an amount of no greater than about 20 wt-%, and more preferably no greater than about 5 wt-%, based on the total weight (including water) of the components of the hardenable composition.

Photoinitiators

Photoinitiators can also be added to the hardenable composition, but are not required. The photoinitator should be capable of promoting free radical crosslinking of the ethylenically unsaturated component on exposure to light of a suitable wavelength and intensity. It also preferably is sufficiently shelf-stable and free of undesirable coloration to permit its storage and use under typical dental conditions. Visible light photoinitiators are preferred. The photoinitiator preferably is miscible with the resin system, and more preferably water-soluble or water-miscible. Photoinitiators bearing polar groups usually have a sufficient degree of water-solubility or water-miscibility. The photoinitiator frequently can be used alone but typically it is used in combination with a suitable donor compound or a suitable accelerator (for example, amines, peroxides, phosphorus compounds, ketones and alpha-diketone compounds).

Suitable visible light-induced and ultraviolet light-induced initiators will be familiar to those skilled in the art. Preferred visible light-induced initiators include camphorquinone, diaryliodonium simple or metal complex salts, chromophore-substituted halomethyl-s-triazines and halomethyl oxadiazoles. Particularly preferred visible light-induced photoinitiators include combinations of an alpha-diketone such as camphorquinone, and a diaryliodonium salt such as diphenyliodonium chloride, bromide, iodide or hexafluorophosphate. Preferred ultraviolet light-induced polymerization initiators include amines that are optionally polymerizable.

If employed, the photoinitiator should be present in an amount sufficient to provide the desired rate of photopolymerization. This amount will be dependent in part on the light source, the thickness of the layer of the composition to be exposed to radiant energy and the extinction coefficient of the photoinitiator.

Preferably, mixed but unset photocurable compositions of the invention include at least about 0.01 wt-%, and more preferably at least about 0.1 wt-%, based on the total weight (including water) of the hardenable (mixed but unset) composition. Preferably, mixed but unset photocurable compositions of the invention include no greater than about 5 wt-%, and more preferably no greater than about 2 wt-%, based on the total weight (including water) of the hardenable (mixed but unset) composition.

Water

The compositions of the invention contain water. The water can be distilled, deionized, or plain tap water. Generally, deionized water is preferred.

The amount of water should be sufficient to provide adequate handling and mixing properties and to permit the transport of ions, particularly in the filler-acid reaction. Preferably, water represents at least about 2 wt-%, and more preferably at least about 5 wt-%, of the total weight of ingredients used to form the composition. Preferably, water represents no greater than about 90 wt-%, and more preferably no greater than about 80 wt-%, of the total weight of ingredients used to form the composition.

Optional Additives

Optionally, the hardenable compositions also may contain solvents (e.g., alcohols) or diluents other than water. If desired, the hardenable composition of the invention can contain adjuvants such as pigments, inhibitors, accelerators, viscosity modifiers, surfactants, and other ingredients that will be apparent to those skilled in the art.

Preparation and Use of the Compositions

The compositions of the present invention are adjusted to provide an appropriate balance of properties in the hardenable composition, both during the setting reaction and after the composition has hardened. These properties include the color stability, the toxicity and the reaction time ("snap set") of the cured composition, along with the shelf stability of the components of the hardenable composition. For example, the hardenable composition should preferably have a snap set of less than or equal to about two (2) minutes for a dental application. The total set time of a composition (i.e., the time for a hardenable resin to cure from a liquid or paste state into a solid material under moisture and temperature conditions similar to those within an oral cavity) is preferably less than about 6 minutes, and more preferably less than about 4 minutes.

The hardenable compositions of the invention can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the polymerizable reducing agent is present in one part of the system, then the oxidizing agent is typically present in anotherpart of the system. However, the polymerizable reducing agent and oxidizing agent can be combined in the same part of the system through the use of the microencapsulation technique.

The components of the hardenable composition can be included in a kit, where the contents of the composition are packaged, as described below, to allow for storage of the components until they are needed.

When used as a dental composition, the components of the hardenable compositions can be mixed and clinically applied using conventional techniques. A curing light is not required (unless a photoinitiator has been included in the composition). The compositions can provide very good adhesion to dentin and/or enamel, without requiring hard tissue pretreatment. Alternatively, a primer layer can be used on the tooth tissue on which the hardenable composition is used. The compositions can also provide very good long-term fluoride release. Hence the compositions of the invention may provide glass ionomer cements that can be cured in bulk without the application of light or other external curing energy, do not require a pre-treatment, have improved physical properties including improved flexural strength, and have high fluoride release for cariostatic effect.

The compositions of the invention are particularly well adapted for use as a wide variety of dental materials, which may be filled or unfilled. They can be used in sealants or adhesives, which are lightly filled composites (up to about 25 wt-% filler, based on the total weight of the composition) or unfilled compositions that are cured after being dispensed adjacent to a tooth (i.e., placing a dental material in temporary or permanent bonding or touching contact with a tooth). They can be used in cements, which are typically filled compositions (preferably containing greater than about 25 wt-% filler and up to about 60 wt-% filler). They can also be used in restoratives, which are composites that are polymerized after being disposed adjacent to a tooth, such as filling materials. They can also be used in prostheses, which are composites that are shaped and polymerized for final use (e.g., as a crown, bridge, veneer, inlay, onlay, or the like), before being disposed adjacent to a tooth. Such preformed articles can be ground or otherwise formed into a custom-fitted shape by the dentist or other user.

The compositions have particular utility in clinical applications where cure of conventional light-curable cement may be difficult to achieve. Such applications include, but are not limited to, deep restorations, large crown build-ups, endodontic restorations, attachment of orthodontic brackets (including pre-coated brackets, where, for example, a paste portion could be pre-applied to the bracket and a liquid portion could later be brushed onto a tooth), bands, buccal tubes, and other devices, luting of metallic crowns or other light-impermeable prosthetic devices to teeth, and other restorative applications in inaccessible areas of the mouth.

For preferred embodiments, the combination of an ionic hardening reaction between the FAS glass and acidic polymer, plus a separate redox curing dark reaction, facilitates thorough, uniform cure and retention of good clinical properties. The compositions of the invention thus show good promise as a universal restorative.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis and all water is deionized water.

EXAMPLES

Abbreviations, Descriptions, and Sources of Materials

| Abbreviation | Description | Source |
| --- | --- | --- |
| Bis-GMA | 2,2-Bis[4-(2-hydroxy-3-methacryloyloxy-propoxy)phenyl]propane | CAS No. 1565-94-2 |
| TBDMA | 4-tert-Butyl dimethylaniline | Sigma-Aldrich, St. Louis, MO |
| BHT | 2,6-Di-tert-butyl-4-methylphenol | Sigma-Aldrich |
| A174 | γ-Methacryloxypropyl trimethoxysilane | Witco Osi Specialties, Danbury, CT |
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity ρ = 4.64. | |
| IEM | 2-Isocyanatoethyl methacrylate | Sigma-Aldrich |
| AA:ITA:IEM | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. | |
| ATU | Allylthiourea | Sigma-Aldrich |
| HEMA | 2-Hydroxyethyl methacrylate; contains 150 ppm 4-methoxyphenol as an inhibitor. | Sigma-Aldrich |
| KDHP | Potassium dihydrogen phosphate | Sigma-Aldrich |

-continued

| Abbreviation | Description | Source |
| --- | --- | --- |
| KS | Potassium sulfate | Sigma-Aldrich |
| KPS | Potassium persulfate | Sigma-Aldrich |
| AEROSIL R812S | Fumed silica | Degussa Corp., Akron, OH |
| CsS | Cesium sulfate | Sigma-Aldrich |
| CsPS | Cesium persulfate | CAS No. 29287-69-2 |
| FAS A | A fluoroaluminasilicate (FAS) glass powder like the "Control Glass" of Example 1 of U.S. Pat. No. 5,154,762 (Mitra et al.) (but having a surface area of 2.8 $m^2/g$) was silane-treated with a liquid treatment solution. The treatment solution had been prepared by combining 4 parts A174 γ-methacryloxypropyl trimethoxysilane (CK Witco Corp., Greenwich, CT) and 60 parts water, adding glacial acetic acid to obtain a pH of 3.01, and stirring for 0.5 hours. The resulting clear treatment solution was mixed with 100 parts of the glass powder and an additional 67 parts of water to provide a slurry. The pH of the slurry was adjusted to 7.0 by adding 5% ammonium hydroxide. After 30 minutes of additional stirring, the mixture was poured into a tray lined with TEFLON polytetrafluoroethylene (DuPont, Wilmington, DE) and dried for 24 hours at 95° C. The resulting dried cake was crushed by sifting it through a 74-micrometer sieve. | |
| FAS B | The "Control Glass" of Example 1 of U.S. Pat. No. 5,154,762 was ground to a surface area of 84 $m^2/g$ and silane-treated with a liquid treatment solution. The silane treatment and subsequent process for isolating the dried glass was carried out as described for FAS A, except that 8 parts of A174 γ-methacryloxypropyl trimethoxysilane were used. | |
| Zr-Si Filler | Silane-treated zirconia-silica (Zr-Si) filler was prepared as described in U.S. Pat. No. 4,503,169 (Randklev). | |

Test Methods

Storage Stability: Paste samples (containing an oxidizing agent component) were stored at 37° C. and 45° C. (at 70% relative humidity) and evaluated daily for 3 days and then weekly for their ability to combine and gel (i.e., harden) with a corresponding paste (containing a reducing agent component). A paste sample was determined to be stable if it remained in a non-hardened paste form and if a hardened composition was formed when the paste sample was mixed with the corresponding paste. The number of days at each temperature that the paste samples remained stable was reported.

Compressive strength (CS): Compressive strength was evaluated by first injecting a mixed cement sample into a glass tube having a 4-mm inner diameter. The ends of the glass tube were plugged with silicone plugs. The filled tubes were subjected to 0.275 megapascal (MPa) pressure for 5 minutes, placed in a chamber at 37° C. and greater than 90% relative humidity (RH) and allowed to stand for 1 hour. The cured sample was next placed in 37° C. water for 1 day, and then cut to a length of 8 mm. Compressive strength was determined according to ISO Standard 7489 using an INSTRON universal tester (Instron Corp., Canton, Mass.) operated at a crosshead speed of 1 millimeter per minute (mm/min).

Diametral Tensile Strength (DTS): Diametral tensile strength was measured using the above-described CS procedure, but using samples cut to a length of 2 mm.

Dentin Adhesion (DA): Dentin adhesion was measured according to the procedure described in U.S. Pat. No. 5,154,762, but without using any pretreatment of the dentin.

Enamel Adhesion (EA): Enamel adhesion was measured according to the procedure described in U.S. Pat. No. 5,154,762.

Working Time: The working time for a mixed paste-paste cement to solidify was measured according to the following procedure. The tools and pastes were stored before use in a constant temperature and humidity room (22° C. and 50% RH) and the procedure was conducted in the same room. Selected amounts of A and B pastes were mixed by a spatula on a pad for 25 seconds (sec) and the resulting mixed composition sample transferred into the semi-cylindrical trough section (8-cm long, 1-cm wide and 3-mm deep) of an 8-cm by 10-cm plastic block. At time 1:00 min, perpendicular grooves were made using a ball point (1-mm diameter) groove maker across the trough every 30 sec; at 2:00 min, the grooves were made every 15 sec; and, closer to the end of the working time, the grooves were made every 10 sec. The end of the working time was determined when the lumps of the cement sample moved with the groove maker. The working time was reported as the average of 2 or 3 measurements.

Example 1

First Paste Compositions and Stability Evaluations

The objective of this example was to evaluate the storage stability of various first paste compositions containing potassium persulfate (KPS) as an oxidizing agent, various levels of water, and various levels of other potassium salts, i.e., potassium sulfate (KS) and potassium dihydrogen phosphate (KDHP), as potential stabilizing agents. Seven first paste compositions (designated with the letter A as A1 through A7) were prepared by combining the ingredients (indicated as percent by weight) as listed in Table 1. The pastes were aged according to the Storage Stability Test Method described herein and the results are included at the bottom of Table 1.

TABLE 1

First Paste Compositions and Storage Stability Results

| Ingredient | Paste A1 | Paste A2 | Paste A3 | Paste A4 | Paste A5 | Paste A6 | Paste A7 |
|---|---|---|---|---|---|---|---|
| Water | 6.9 | 6.8 | 11.5 | 11.4 | 11.2 | 15.0 | 11.6 |
| KDHP | 0 | 0 | 0 | 0 | 2.6 | 0 | 0 |
| KS | 0 | 1.2 | 0 | 1.1 | 0.8 | 0 | 0 |
| CsS | 0 | 0 | 0 | 0 | 0 | 0 | 17.7 |
| HEMA | 24.2 | 23.9 | 18.9 | 18.7 | 18.3 | 18.6 | 14.4 |
| BHT | 0.076 | 0.075 | 0.079 | 0.078 | 0.076 | 0.07 | 0.055 |
| AA:ITA:IEM | 38.1 | 37.6 | 42 | 41.5 | 40.6 | 41.0 | 31.8 |
| BisGMA | 3.5 | 3.4 | 3.6 | 3.6 | 3.5 | 0 | 0 |
| KPS | 2.5 | 2.1 | 2.4 | 2.4 | 2.3 | 0 | 0 |
| CsPS | 0 | 0 | 0 | 0 | 0 | 4.5 | 3.5 |
| Zr-Si Filler | 24.2 | 23.9 | 21 | 20.8 | 20.3 | 20.3 | 20.5 |
| Aerosil R812S | 0.5 | 1.0 | 0.5 | 0.5 | 0.5 | 0.5 | 0.5 |

Storage Stability Results

| Temperature | Days Stable (A "+" sign indicates that the sample was still stable at that time.) | | | | | | |
|---|---|---|---|---|---|---|---|
| 37° C. | 27 | 208+ | 2 | — | 109+ | 1 | 150+ |
| 45° C. | 1 | 65+ | 1 | 3 | 65+ | — | — |

Set Time: The set time for a curable paste-paste sample to cure from a paste state into a solid material was measured according to the following procedure. In a constant temperature and humidity room (22° C. and 50% RH), one gram each of pastes A and B were vigorously spatulated for 25 seconds. A cubic aluminum mold having a rectangular hole (10-mm long, 8-mm wide and 5-mm deep) through the center was then completely filled with the mixed paste material. The filled mold was then placed with one filled end (the bottom end) on a polyester film that covered an aluminum pad. After 45 seconds (from time of initial mixing), another polyester film was placed on the top filled end of the mold and a 400-gram standard weight was placed on top of the film. At time 90 seconds, the weight was removed and the sandwiched sample construction was transferred to a 95% RH and 37° C. humidity chamber. At time 120 seconds, the top polyester film was removed and the top surface of the curing paste material was manually indented with an indenter device consisting of a cylindrical "needle" having a flat point at one end and connected to a 400-gram block of material at the handle end. The test sample was indented every 10–15 seconds until the needle end did not hit the film-covered aluminum pad. The elapsed time from the start of mixing until the last touch of the needle with the bottom plate was defined as set time. The set time was reported an average of 2 or 3 measurements.

It can be concluded from the data in Table 1 that (1) the addition of KS significantly increased the storage stability of first paste samples containing "low" amounts (about 7%) of water (compare Paste A2 with Paste A1); (2) the addition of a similar amount of KS only marginally increased the storage stability of first paste samples containing "high" amounts (about 11%) of water (compare Paste A4 with Paste A3); (3) the addition of higher levels of mixed KDHP and KS salts significantly increased the storage stability of first paste samples containing "high" amounts (about 11%) of water (compare Paste A5 with Pastes A3 and A4); and (4) the addition of CsS significantly increased the storage stability of first paste samples containing CsPS as the oxidizing agent. (compare Pastes A6 and A7).

Example 2

Second Paste Compositions and Evaluations of Paste-Paste Curing

The objective of this example was to evaluate the cure rates of cements prepared from combining the first pastes of Example 1 (containing an oxidizing agent component) with corresponding second pastes that contained a reducing agent component. Two second paste compositions (designated with the letter B as B1 and B2) were prepared by combining the ingredients (indicated as percent by weight) as listed in Table 2.

TABLE 2

Second Paste Compositions

| Ingredient | Paste B1 | Paste B2 |
|---|---|---|
| Water | 13.6 | 11.4 |
| HEMA | 8.7 | 10.3 |
| ATU | 1.4 | 1.4 |
| TBDMA | 0.16 | 0.16 |
| FAS I | 37.2 | 37.6 |
| FAS II | 37.2 | 37.6 |
| $TiO_2$ | 0.5 | 0.5 |
| Aerosil R812S | 1.2 | 1.1 |

Cements were prepared by spatulating 2.3 g of a freshly prepared first paste with 1.0 g of a freshly prepared second paste for 25 seconds. The resulting materials were evaluated for Compressive Strength (DS), Diametral Strength (DTS), Adhesion to Dentin (DA), Adhesion to Enamel (EA), Working Time, and Set Time according to the Test Methods described herein and the results are reported in Table 3.

TABLE 3

Curing Results and Cement Physical Properties

| Test | Paste A1 + Paste B1 | Paste A2 + Paste B1 | Paste A3 + Paste B2 | Paste A4 + Paste B2 | Paste A5 + Paste B2 |
|---|---|---|---|---|---|
| CS, MPa | 93 | 130 | 132 | NA | 130 |
| DTS, MPa | 19.4 | 19.6 | 22.1 | NA | 24.1 |
| DA, MPa | 2.0 | 1.8 | 2.5 | 2.5 | 3.5 |
| EA, MPa | 5.0 | 6.5 | 6.5 | 6.0 | 8.5 |
| Working Time Minutes:Seconds | 2:00 | 2:40 | 1:20 | 1:15 | 3:20 |
| Set Time Minutes:Seconds | 2:30 | 2:40 | 1:20 | 1:20 | 2:50 |

NA = Not Evaluated

It can be concluded from the results from Table 3 that the added salts do not compromise the curing times or physical properties of the resulting cements.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by the way of example only with the scope of the invention intended to be limited only by the claims set forth herein as follows.

What is claimed is:

1. A multi-part hardenable medical composition, wherein at least one part comprises:
   a hardenable resin system comprising an ethylenically unsaturated component; water;
   an ionic reducing agent or an ionic oxidation agent; and
   a secondary ionic salt comprising a cation selected from the group consisting of a Group I ion, a Group II ion, an ammonium ion of the formula $NR_4^+$ wherein each R is H or a (C1–C4)alkyl group, and mixtures thereof;
   wherein the at least one part has increased shelf life relative to the same part without the secondary ionic salt.

2. The hardenable medical composition of claim 1 which is an adhesive.

3. The hardenable medical composition of claim 2 wherein the adhesive includes up to about 25 wt-% filler.

4. The hardenable medical composition of claim 1 which is a sealant.

5. The hardenable medical composition of claim 1 wherein the secondary ionic salt comprises a Group Ia ion.

6. The hardenable medical composition of claim 1 wherein the at least one part comprises an ionic oxidizing agent and at least one another part comprises a reducing agent.

7. The hardenable medical composition of claim 1 wherein the at least one part comprises an ionic reducing agent and at least one other part comprises an oxidizing agent.

8. The hardenable medical composition of claim 1 wherein the ionic reducing agent is polymerizable or non-polymerizable.

9. The hardenable medical composition of claim 1 wherein the hardenable resin system further comprises an acid-functional component.

10. The hardenable medical composition of claim 1 further comprising a photoinitiator.

11. A multi-part hardenable medical composition, wherein at least one part comprises:
    a hardenable resin system comprising an ethylenically unsaturated component;
    water;
    a filler;
    an ionic reducing agent or an ionic oxidation agent; and
    a secondary ionic salt comprising a cation selected from the group consisting of a Group I ion, a Group II ion, an ammonium ion of the formula $NR_4^+$ wherein each R is H or a (C1–C4)alkyl group, and mixtures thereof;
    wherein the at least one part has increased shelf life relative to the same part without the secondary ionic salt.

12. The hardenable medical composition of claim 11 wherein the secondary ionic salt comprises a Group Ia ion.

13. The hardenable medical composition of claim 11 wherein the ionic reducing agent is polymerizable or non-polymerizable.

14. The hardenable medical composition of claim 11 wherein the at least one part comprises an ionic oxidizing agent and at least one other part comprises a reducing agent.

15. The hardenable medical composition of claim 14 wherein the at least one part comprises a urea- or thiourea-containing reducing agent.

16. The hardenable medical composition of claim 15 wherein the reducing agent is nonpolymerizable.

17. The hardenable medical composition of claim 16 wherein the reducing agent is selected from the group consisting of 1-ethyl-2-thiourea, tetraethyl thiourea, tetramethyl thiourea, 1,1-dibutyl thiourea, 1,3-dibutyl thiourea, and mixtures thereof.

18. The hardenable medical composition of claim 14 wherein the reducing agent is polymerizable or nonpolymerizable.

19. The hardenable medical composition of claim 11 wherein the at least one part comprises an ionic reducing agent and at least one other part comprises an oxidizing agent.

20. The hardenable medical composition of claim 19 wherein the oxidizing agent is selected from the group consisting of a persulfuric acid, persulfuric acid salt, peroxide, hydroperoxide, transition metal salt, perboric acid, perboric acid salt, permanganic acid, permanganic acid salt, perphosphoric acid, perphosphoric acid salt, and mixtures thereof.

21. The hardenable medical composition of claim 18 wherein the reducing agent is polymerizable.

22. The hardenable medical composition of claim 21 wherein the polymerizable reducing agent comprises a urea or thiourea functional group.

23. The hardenable medical composition of claim 22 wherein the polymerizable reducing agent is selected from the group consisting of 5-acryloxyalkyl barbituric acid, 5-allyl 5-isopropyl barbituric acid, 5-ethyl 5-crotyl barbituric acid, a (meth)acryloxyalkyl thiourea, 1-allyl thiourea, 1,1-diallyl thiourea, 1,3-diallyl thiourea, 1-allyl-3-(2-hydroxyethyl)-2-thiourea, 1-allyl-3-methyl thiourea, and mixtures thereof.

24. The hardenable medical composition of claim 22 wherein the at least one other part further comprises a secondary reducing agent that is polymerizable or nonpolymerizable.

25. The hardenable medical composition of claim 11 wherein the hardenable resin system further comprises an acid-functional component.

26. The hardenable medical composition of claim 25 wherein the acid-functional component comprises a homopolymer or copolymer of alkenoic acids.

27. The hardenable medical composition of claim 25 wherein the filler is a finely divided acid-reactive filler.

28. The hardenable medical composition of claim 25 wherein the acid-functional component and ethylenically unsaturated component are the same component.

29. The hardenable medical composition of claim 28 wherein the acid-functional component and ethylenically unsaturated component comprise an α,β-unsaturated acidic compound selected from the group consisting of glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly (meth)acrylated poly(meth)acrylic acid, poly(meth) acrylated polycarboxyl-polyphosphonic acid, poly(meth) acrylated polychlorophosphoric acid, poly(meth)acrylated polysulfonate, poly(meth)acrylated polyboric acid, and mixtures thereof.

30. The hardenable medical composition of claim 11 wherein the ethylenically unsaturated component is selected from the group consisting of an acrylate, a methacrylate, an acrylamide, a methacrylamide, a urethane acrylate, a urethane methacrylate, and mixtures thereof.

31. The hardenable medical composition of claim 30 wherein the ethylenically unsaturated component is selected from the group consisting of 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, triethylene glycol dimethacrylate, bisGMA, ethoxylated bisphenolA diacrylate, ethoxylated bisphenolA dimethacrylate, polyethylene glycol dimethacrylate, urethane methacrylates, acrylamide, methacrylamide, methylene bis-acrylamide, methylene bis-methacrylamide, diacetone acrylamide, diacetone methacrylamide, and mixtures thereof.

32. The hardenable medical composition of claim 11 wherein the at least one part comprises an ionic oxidizing agent selected from the group consisting of a persulfuric acid salt, transition metal salt, perboric acid salt, permanganic acid salt, perphosphoric acid salt, and mixtures thereof.

33. The hardenable medical composition of claim 11 further comprising a photoinitiator.

34. The hardenable medical composition of claim 11 which is a dental sealant, dental adhesive, dental cement, dental restorative, or a dental prostheses.

35. A multi-part hardenable dental composition, wherein at least one part comprises:
a hardenable resin system comprising an ethylenically unsaturated component and an acid-functional component;
water;
an acid-reactive filler;
an ionic oxidizing agent; and
a secondary ionic salt comprising a cation selected from the group consisting of a Group I ion, a Group II ion, an ammonium ion of the formula $NR_4^+$ wherein each R is H or a (C1–C4)alkyl group, and mixtures thereof;
wherein the at least one part has increased shelf life relative to the same part without the secondary ionic salt.

36. The hardenable dental composition of claim 35 which is a dental sealant, dental adhesive, dental cement, dental restorative, or a dental prostheses.

37. A kit for forming a medical composition, the kit comprising at least one container comprising a composition comprising:
a hardenable resin system comprising an ethylenically unsaturated component;
water;
an ionic reducing agent or an ionic oxidation agent; and
a secondary ionic salt comprising a cation selected from the group consisting of a Group I ion, a Group II ion, an ammonium ion of the formula $NR_4^+$ wherein each R is H or a (C1–C4)alkyl group, and mixtures thereof;
wherein the composition in the at least one container has increased shelf life relative to the same composition without the secondary ionic salt.

38. The kit of claim 37 further comprising a filler.

39. The kit of claim 37 wherein the medical composition is a dental sealant, dental adhesive, dental cement, dental restorative, or a dental prostheses.

40. A method of making a multi-part hardenable medical composition, the method comprising:
proving a hardenable resin system comprising an ethylenically unsaturated component;
providing water;
providing an ionic oxidizing agent or an ionic reducing agent;
providing a secondary ionic salt comprising a cation selected from the group consisting of a Group I ion, a Group II ion, an ammonium ion of the formula $NR_4^+$ wherein each R is H or a (C1–C4)alkyl group, and mixtures thereof; and
mixing the resin system, the water, the ionic oxidizing agent or ionic reducing agent, and the secondary ionic salt to form at least one part of the composition; wherein the at least one part has increased shelf life relative to the same part without the secondary ionic salt.

41. The method of claim 40 further comprising providing a filler and mixing the filler with the resin system, the water, the ionic oxidizing agent or ionic reducing agent, and the secondary ionic salt to form the at least one part.

42. A method of adhering a dental article to a tooth or bone, the method comprising:
providing a multi-part hardenable dental composition, wherein at least one part comprises:
a hardenable resin system comprising an ethylenically unsaturated component;
water;
an ionic oxidizing agent or ionic reducing agent; and
a secondary ionic salt comprising a cation selected from the group consisting of a Group I ion, a Group II ion, an ammonium ion of the formula $NR_4^+$ wherein each R is H or a (C1–C4)alkyl group, and mixtures thereof; wherein the at least one part has increased shelf life relative to the same part without the secondary ionic salt; and
adhering the dental article to the tooth or bone using the hardenable composition.

43. A method of cementing a dental article to a tooth or bone, the method comprising:
providing a mulit-part hardenable dental composition, wherein at least one part comprises:
a hardenable resin system comprising an ethylenically unsaturated component;
water;
a filler;
an ionic oxidizing agent or ionic reducing agent; and
a secondary ionic salt comprising a cation selected from the group consisting of a Group I ion, a Group II ion, an ammonium ion of the formula $NR_4^+$ wherein each R is H or a (C1–C4)alkyl group, and mixtures thereof; wherein the at least one part has increased shelf life relative to the same part without the secondary ionic salt; and
cementing the dental article to the tooth or bone using the hardenable composition.

44. A method of filling a tooth, the method comprising:
providing a multi-part hardenable dental composition, wherein at least one part comprises:
a hardenable resin system comprising an ethylenically unsaturated component;
water;
an ionic redox polymerization system comprising an ionic oxidizing agent, a reducing agent comprising a urea or thiourea functional group; and
a secondary ionic salt comprising a cation selected from the group consisting of a Group I ion, a Group II ion, an ammonium ion of the formula $NR_4^+$ wherein each R is H or a (C1–C4)alkyl group, and mixtures thereof; wherein the at least one part has increased shelf life relative to the same part without the secondary ionic salt; and
applying the hardenable composition to the tooth.

45. The hardenable medical composition of claim 6 wherein the reducing agent is polymerizable or nonpolymerizable.

* * * * *

UNITED STATES PATENT AND TRADEMARK OFFICE
CERTIFICATE OF CORRECTION

PATENT NO. : 6,982,288 B2
APPLICATION NO. : 10/121329
DATED : January 3, 2006
INVENTOR(S) : Mitra, Sumita B.

It is certified that error appears in the above-identified patent and that said Letters Patent is hereby corrected as shown below:

Column First Page Col. 2 (U.S. Patent Documents) – Line 1 - Delete "Schnafke" and insert - - Schnalke - -, therefor.

Column 12 – Line 40 (Approx.) - Delete "anotherpart" and insert - - another part - -, therefor.

Column 17 – Line 53 - After "by" delete "the".

Column 18 – Line 15 - In claim 6, delete "another" and insert - - other - -, therefor.

Column 22 – Line 3 - In Claim 43, delete "mulit-part" and insert - - multi-part - -, therefor.

Signed and Sealed this

Eighth Day of August, 2006

JON W. DUDAS
*Director of the United States Patent and Trademark Office*